(12) United States Patent
Lands et al.

(10) Patent No.: US 6,887,240 B1
(45) Date of Patent: May 3, 2005

(54) VESSEL SEALING WAVE JAW

(75) Inventors: Michael J. Lands, Louisville, CO (US); Stephen Wade Lukianow, Boulder, CO (US); Steven P. Buysse, Longmont, CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/419,592

(22) Filed: Oct. 18, 1999

Related U.S. Application Data (63) Continuation-in-part of application No. 09/104,729, filed on Jun. 25, 1998, now Pat. No. 6,179,834, which is a continuation-in-part of application No. 08/530,450, filed on Sep. 19, 1995, now Pat. No. 5,776,130.
(60) Provisional application No. 60/105,333, filed on Oct. 23, 1998.

(51) Int. Cl.[7] ............................................... A61B 18/18
(52) U.S. Cl. ............................ 606/51; 606/52; 606/207
(58) Field of Search .................................. 606/207, 151, 606/48, 50, 56, 205, 206, 208, 209, 51, 52, 45, 49, 210, 211; 128/751; 81/424.5, 418, 426, 42.65

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 2,002,594 A | 5/1935 | Wappler et al. |
| 2,176,479 A | 10/1939 | Willis |
| 2,397,823 A * | 4/1946 | Walter .......................... 606/207 |
| 2,518,994 A | 8/1950 | Miller |

(Continued)

FOREIGN PATENT DOCUMENTS

| | | | |
|---|---|---|---|
| CA | 2104423 | 2/1994 | |
| DE | 19608716 | 4/1997 | |
| EP | 0572131 A1 | 12/1993 | |
| EP | 0 584 787 A1 | 3/1994 | |
| EP | 0 584 787 A1 * | 3/1994 | ........... A61B/17/28 |
| EP | 0 853 922 A1 | 7/1998 | |
| SU | 401367 | 10/1973 | |
| WO | WO 01/54604 A1 | 8/2001 | |
| WO | WO 02/060798 A1 | 10/2002 | |

OTHER PUBLICATIONS

US 6,090,109, 7/2000, Lands et al. (withdrawn)*
Sigel et al., "The Mechanism of Blood Vessel Closure by High Frequency Electrocoagulation." Surgery Gynecology & Obstretrics, Oct. 1965, pp. 823–831.

(Continued)

*Primary Examiner*—Eduardo C. Robert (57) ABSTRACT

A forceps for clamping, grasping, manipulating, coagulating/desiccating and cutting tissue includes a shaft portion having a proximal end, a distal end and first and second jaw members pivotally attached to the distal end of the shaft by a pivot assembly. Each of the jaw members including an opposing inner facing surface having a plurality of wave forms disposed thereon for engaging tissue therebetween. The wave forms disposed on the inner facing surface of the second jaw member being complimentary to the wave forms on the inner facing surface of first jaw member. A handle portion having an actuating assembly is attached to the proximal end of the shaft for imparting movement of the first and second jaw members from a first open position wherein the jaw members are disposed in spaced relation relative to one another to a second clamping position wherein the jaw members cooperate to grasp tissue therebetween. One embodiment of the forceps includes a pair of electrodes clamped on the inner facing surface of each jaw member for imparting electrosurgical energy to the tissue grasped therebetween.

9 Claims, 9 Drawing Sheets

U.S. PATENT DOCUMENTS

| | | |
|---|---|---|
| 3,404,677 A | 10/1968 | Springer |
| 3,515,139 A | 6/1970 | Malina |
| 3,643,663 A | 2/1972 | Sutter |
| 3,651,811 A | 3/1972 | Hildebrandt et al. |
| 3,895,636 A | 7/1975 | Schmidt |
| 3,920,021 A | 11/1975 | Hiltebrandt |
| 3,938,527 A | 2/1976 | Rioux et al. |
| 3,952,749 A | 4/1976 | Fridolph et al. |
| 3,980,861 A * | 9/1976 | Fukunaga .................... 219/230 |
| 4,005,714 A | 2/1977 | Hiltebrandt |
| 4,370,980 A | 2/1983 | Lottick |
| 4,492,231 A | 1/1985 | Auth |
| 4,552,143 A | 11/1985 | Lottick |
| 4,597,379 A | 7/1986 | Xihn et al. |
| 4,671,274 A | 6/1987 | Sorochenko |
| 4,685,459 A | 8/1987 | Xoch et al. |
| 4,763,669 A | 8/1988 | Jaeger |
| 4,836,205 A | 6/1989 | Barrett |
| 4,887,612 A | 12/1989 | Esser et al. |
| 4,938,761 A | 7/1990 | Ensslin |
| 5,026,370 A | 6/1991 | Lottick |
| 5,116,332 A | 5/1992 | Lottick |
| 5,147,356 A | 9/1992 | Bhatta |
| 5,151,102 A | 9/1992 | Xamiyama et al. |
| 5,197,493 A | 3/1993 | Grier-Idris |
| 5,199,441 A | 4/1993 | Hogle |
| 5,217,458 A | 6/1993 | Parins |
| 5,217,460 A | 6/1993 | Knoepfler |
| 5,250,047 A | 10/1993 | Rydell |
| 5,258,006 A | 11/1993 | Rydell et al. |
| 5,263,967 A | 11/1993 | Lyons, III et al. |
| 5,275,615 A * | 1/1994 | Rose .......................... 606/208 |
| 5,277,201 A | 1/1994 | Stern |
| 5,282,800 A | 2/1994 | Foshee et al. |
| 5,282,826 A | 2/1994 | Quadri |
| 5,304,203 A | 4/1994 | El-Mallawany et al. |
| 5,324,289 A | 6/1994 | Eggers |
| 5,330,471 A | 7/1994 | Eggers |
| 5,336,221 A | 8/1994 | Anderson |
| 5,342,359 A | 8/1994 | Rydell |
| 5,342,389 A | 8/1994 | Haber et al. |
| 5,352,222 A | 10/1994 | Rydell |
| 5,356,408 A | 10/1994 | Rydell |
| 5,372,589 A | 12/1994 | Davis |
| 5,389,104 A | 2/1995 | Hahnen et al. |
| 5,391,166 A | 2/1995 | Eggers |
| 5,403,312 A | 4/1995 | Yates et al. |
| 5,431,674 A | 7/1995 | Basile et al. |
| 5,443,463 A | 8/1995 | Stern et al. |
| 5,443,464 A | 8/1995 | Russell et al. |
| 5,443,479 A | 8/1995 | Bressi, Jr. |
| 5,445,658 A | 8/1995 | Durrfeld et al. |
| 5,456,684 A * | 10/1995 | Schmidt et al. ............... 606/41 |
| 5,458,598 A | 10/1995 | Feinberg et al. |
| 5,462,546 A | 10/1995 | Rydell |
| 5,472,443 A | 12/1995 | Cordis et al. |
| 5,478,351 A | 12/1995 | Meade et al. |
| 5,484,436 A | 1/1996 | Eggers et al. |
| 5,486,172 A | 1/1996 | Chess |
| 5,507,772 A | 4/1996 | Shutt et al. |
| 5,509,922 A | 4/1996 | Aranyi et al. |
| 5,527,313 A | 6/1996 | Scott et al. |
| 5,531,744 A | 7/1996 | Nardella et al. |
| 5,540,684 A | 7/1996 | Hassler, Jr. |
| 5,549,623 A | 8/1996 | Sharpe et al. |
| 5,553,624 A * | 9/1996 | Francese et al. ............ 128/751 |
| 5,558,672 A | 9/1996 | Edwards et al. |
| 5,562,720 A | 10/1996 | Stern et al. |
| 5,569,241 A | 10/1996 | Edwards |
| 5,569,243 A | 10/1996 | Kortenbach et al. |
| 5,573,535 A | 11/1996 | Viklund |
| 5,615,690 A | 4/1997 | Giurtino et al. |
| 5,618,305 A * | 4/1997 | Lolagne ...................... 606/205 |
| 5,626,578 A | 5/1997 | Tihon |
| 5,637,110 A | 6/1997 | Pennybacker et al. |
| 5,658,281 A | 8/1997 | Heard |
| 5,667,526 A | 9/1997 | Levin |
| 5,674,220 A | 10/1997 | Fox et al. |
| 5,683,388 A | 11/1997 | Slater |
| 5,693,051 A | 12/1997 | Schulze et al. |
| 5,700,261 A | 12/1997 | Brinkerhoff |
| 5,700,276 A | 12/1997 | Benecke |
| 5,702,390 A | 12/1997 | Austin et al. |
| 5,709,707 A | 1/1998 | Lock et al. |
| 5,720,744 A | 2/1998 | Eggleston et al. |
| 5,728,160 A | 3/1998 | Draenert |
| 5,730,752 A | 3/1998 | Alden et al. |
| 5,735,848 A | 4/1998 | Yates et al. |
| 5,755,717 A | 5/1998 | Yates et al. |
| 5,766,166 A | 6/1998 | Hooven |
| 5,769,849 A | 6/1998 | Eggers |
| 5,776,128 A | 7/1998 | Eggers |
| 5,776,130 A * | 7/1998 | Buysee et al. ................ 606/48 |
| 5,779,701 A | 7/1998 | McBrayer et al. |
| 5,797,958 A | 8/1998 | Yoon |
| 5,810,802 A | 9/1998 | Panescu et al. |
| 5,810,811 A | 9/1998 | Yates et al. |
| 5,817,091 A | 10/1998 | Nardella et al. |
| 5,817,093 A | 10/1998 | Williamson, IV et al. |
| 5,827,281 A | 10/1998 | Levin |
| 5,833,690 A | 11/1998 | Yates et al. |
| 5,893,863 A | 4/1999 | Yoon |
| 5,951,549 A | 9/1999 | Richardson et al. |
| 6,053,933 A | 4/2000 | Balazs et al. |
| 6,083,150 A * | 7/2000 | Aznoian et al. .............. 600/56 |
| H1904 H | 10/2000 | Yates et al. |
| 6,193,718 B1 | 2/2001 | Kortenbach et al. |
| 6,409,728 B1 | 6/2002 | Ehr et al. |
| H2037 H | 7/2002 | Yates et al. |
| 6,443,970 B1 | 9/2002 | Schulze et al. |
| 6,458,128 B1 | 10/2002 | Schulze |
| 6,585,735 B1 | 7/2003 | Frazier et al. |
| 6,620,161 B2 | 9/2003 | Schulze et al. |
| 6,682,528 B2 | 1/2004 | Frazier et al. |
| 2003/0018331 A1 | 1/2003 | Dycus et al. |

OTHER PUBLICATIONS

Bergdahl et al. "Studies on Coagulation and the Development of an Automatic Computerized Bipolar Coagulator", J. Neurosurg, vol. 75, Jul. 1991, pp. 148–151.

International Search Report—PCT/US98/18640.

International Search Report—PCT/US98/23950.

"Innovations in Electrosurgery" Sales/Product Literature.

LigaSure Vessel Sealing System, the Seal of Confidence in General, Gynecologic, Urologic, and Laparaoscopic Surgery Sales/Product Literature.

Carbonell et al., "Comparison of theGyrus PlasmaKinetic Sealer and the ValleyLab LigaSure Device in the Hamostasis of Small, Medium, and Large Sized Arteries" Carolinas Laparoscopic and Advanced Surgery Program, Carolinas Medical Center, Charlotte, NC.

"Reducing Needlestick Injuries in the Operating Room" Sales/Product Literature.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel–Sealing Device for Parenchymal Transaction During Liver Surgery" Journal of Gastrointestinal Surgery, vol. 6, No. 4, Jul./Aug. 2002 pp. 569–574.

Paul G. Hogan, "A Novel Technique for Parenchymal Division During Hepatactomy" The American Journal of Surgery, vol. 161, No. 3, Apr. 2001 pp. 236–237.

W. Scott Halton, "LigaSure Vessel Sealing System: Revolutionary Hamostasis Product for General Surgery" Sales/Product Literature.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hamicolectomy Using the LigaSure Vessel Sealing System" Innovations That Work, Sep. 1999.

Herman et al., "Laparoscopic Intestinal Resection With the LigaSure Vessel Sealing System: A Case Report" Innovations That Work, Feb. 2002.

Carus et al., "Initial Experience With The LigaSure Vessel Sealing System in Abdominal Surgery" Innovations That Work, Jun. 2002.

Levy et al., "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al., "Vessel Sealing For Hemostasis During Gynecologic Surgery" Sales Product Literature.

Sangupta et al., "Line of a Computer–Controlled Bipolar Diathermy System in Radical Prostatactomies and Other Open Urological Surgery" ANZ Journal of Surgery (2001) 71.9, pp. 538–540.

Otsson et al. "Radical Cystectomy in Fernales" Current Surgical Techniques in Urology, vol. 14, Issue 3.

E. David Crawford "Use of a Novel Vessel Sealing Technology in Management of the Dorsal Veinous Complex" Sales Product Literature.

Jarrett et al., "Use of a LigaSure Vessel Sealing System for Perl–Hilar Vessels in Laparoscopic Naphectomy" Sales Product Literature.

E. David Crawford "Evaluation of a New Vessel Sealing Device in Urologic Cancer Surgery" Sales Product Literature.

Joseph Ortenberg "LigaSure System Used in Laparoscopic 1st and 2nd Stage Orchipexy" Innovations That Work, Nov. 2002.

Koyle et al., "Laparoscopic Palamo Varicocele Ligation in Children and Adolescents" Pediatric Endosurgery & Innovative Techniques, vol. 8, No. 1, 2002.

Dulembe et al. "Use of a Bipolar Electrochemical Vessel Sealer in Laparoscopically Assisted Vaginal Hysterectomy" Sales Product Literature.

Johnson et al., "Evaluation of a Bipolar electrothermal Vessel Sealing Device in Hemonholdectomy" Sales Product Literature.

* cited by examiner

VESSEL SEALING WAVE JAW

This application is a continuation-in-part of U.S. application Ser. No. 09/104,729 now U.S. Pat. No. 6,179,834 entitled "VASCULAR TISSUE SEALING PRESSURE CONTROL" which was filed on Jun. 25, 1998 by BUYSSE ET AL., which is a continuation of (U.S. application Ser. No. 08/530,450) now U.S. Pat. No. 5,776,130 which was filed on Sep. 19, 1995 by BUYSSE ET AL. entitled "VASCULAR TISSUE SEALING PRESSURE CONTROL", the entire contents of both of these disclosures are hereby incorporated by reference. This application claims benefit of 60/105,333 filed Oct. 23, 1998.

The present disclosure relates to hemostats or forceps used for open surgical procedures and laparoscopic surgical procedures. More particularly, the present disclosure relates to a fenestrated forceps having wave-like opposing jaws which can be used to apply purely mechanical clamping pressure to clamp, grasp and/or manipulate vascular tissue in an atraumatic fashion or to apply a combination of mechanical clamping pressure and electrosurgical current to cauterize, coagulate/desiccate and/or cut tissue.

TECHNICAL FIELD

A hemostat or forceps is a simple plier-like tool which uses mechanical action between its jaws to constrict vessels and is commonly used in open surgical procedures to grasp, dissect and/or clamp tissue. Electrosurgical forceps are similar clamping devices which utilize both mechanical clamping action and electrical energy to effect hemostasis by heating the tissue and blood vessels to cause coagulation and/or cauterization.

Over the last several decades, more and more surgeons are abandoning traditional open methods of gaining access to vital organs and body cavities in favor of endoscopes and laparoscopic instruments which access organs through small puncture-like incisions. However, due to space limitations surgeons can have difficulty suturing vessels or performing other traditional methods of controlling bleeding, e.g., clamping and/or tying-off transected blood vessels. Electrosurgical instruments and particularly electrosurgical forceps can be used instead to control bleeding.

By utilizing an electrosurgical forceps, a surgeon can either cauterize, coagulate/desiccate and/or cut tissue and/or simply reduce or slow bleeding, by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode. See, e.g., U.S. Pat. Nos. 4,416,276 and 4,416,277 the contents of which are incorporated herein by reference.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

Numerous mechanical and electrosurgical forceps designs have been proposed in the past for various open surgical procedures and laparoscopic surgical procedures. Some of these designs may not provide adequate clamping pressure and/or may cause undue trauma to the tissue during manipulation, clamping and/or coagulation. For example, U.S. Pat. No. 2,518,994 to Miller, U.S. Pat. No. 3,404,677 to Springer and U.S. Pat. No. 5,263,967 to Lyons, III et al. all disclose purely mechanical forceps which have serrated edges or teeth on their respective undersurfaces for grasping and clamping tissue. These structures may have a traumatic effect on delicate tissue. Likewise, U.S. Pat. No. 5,674,220 to Fox et al. and U.S. Pat. No. 5,217,460 to Knoepfler both disclose electrosurgical forceps which also utilize teeth to grasp the tissue and, as a result, may also have a similar traumatic effect on delicate tissue.

Thus, a need exists to develop a forceps which can be utilized effectively without causing needless trauma to tubular vessels or delicate tissues. Preferably, the forceps can be used for both mechanical clamping, grasping and dissecting as well as electrosurgical sealing, coagulation/desiccating and/or cutting of tissue.

SUMMARY

The present disclosure relates to a forceps which includes a shaft portion having a proximal end, a distal end and first and second jaw members pivotally attached to the distal end of the shaft by a pivot assembly. Each of the jaw members includes an opposing inner facing surface having a plurality of wave forms disposed thereon which are capable of engaging tissue therebetween. The plurality of wave forms disposed on the inner facing surface of the second jaw member are complimentary to the plurality of wave forms disposed on the inner facing surface of the first jaw member. The forceps also includes a handle portion attached to the proximal end of the shaft. The handle portion includes an activator assembly disposed therein for imparting movement of the first and second jaw members from a first open position wherein the jaw members are disposed in spaced relation relative to one another to a second clamping position wherein the jaw members cooperate to grasp tissue therebetween.

In one embodiment, the inner facing surfaces of each jaw member include a fenestrated portion disposed therethrough. Preferably, the fenestrated portion of the first jaw member is aligned with the fenestrated portion of the second jaw member.

In another embodiment, the wave forms of the first jaw member include clamping portions and manipulating portions and the wave forms of the second jaw member include complimentary clamping and manipulating portions. Preferably, the plurality of wave forms of each jaw member are longitudinally, transversely and/or both longitudinally and transversely disposed on the inner facing surface of each jaw member.

In yet another embodiment, the manipulating portions of the jaw members include a plurality of teeth which are filleted or rounded to reduce trauma to the tissue. Preferably, the clamping portion of each of the jaw members is wide relative to the manipulating portion to facilitate dissection.

The forceps may be bipolar with each of the inner facing surfaces of the jaw members including an electrode which is connected to a source of electrical energy. The wave forms of the first jaw member include coagulating portions and manipulating portions and the wave forms of the second jaw member include complimentary coagulating and manipulating portions. The source of electrical energy imparts different electrical potentials to each of the electrodes such that the electrodes are capable of conducting bipolar energy through the tissue held between the inner facing surfaces of the jaw members. It is also contemplated that a portion of the inner facing surfaces of each jaw member is non-conductive and/or semi-conductive (i.e., only certain portions of the surface are conductive) to control and/or eliminate current densities at specific jaw locations.

DETAILED DESCRIPTION

Figure 1:
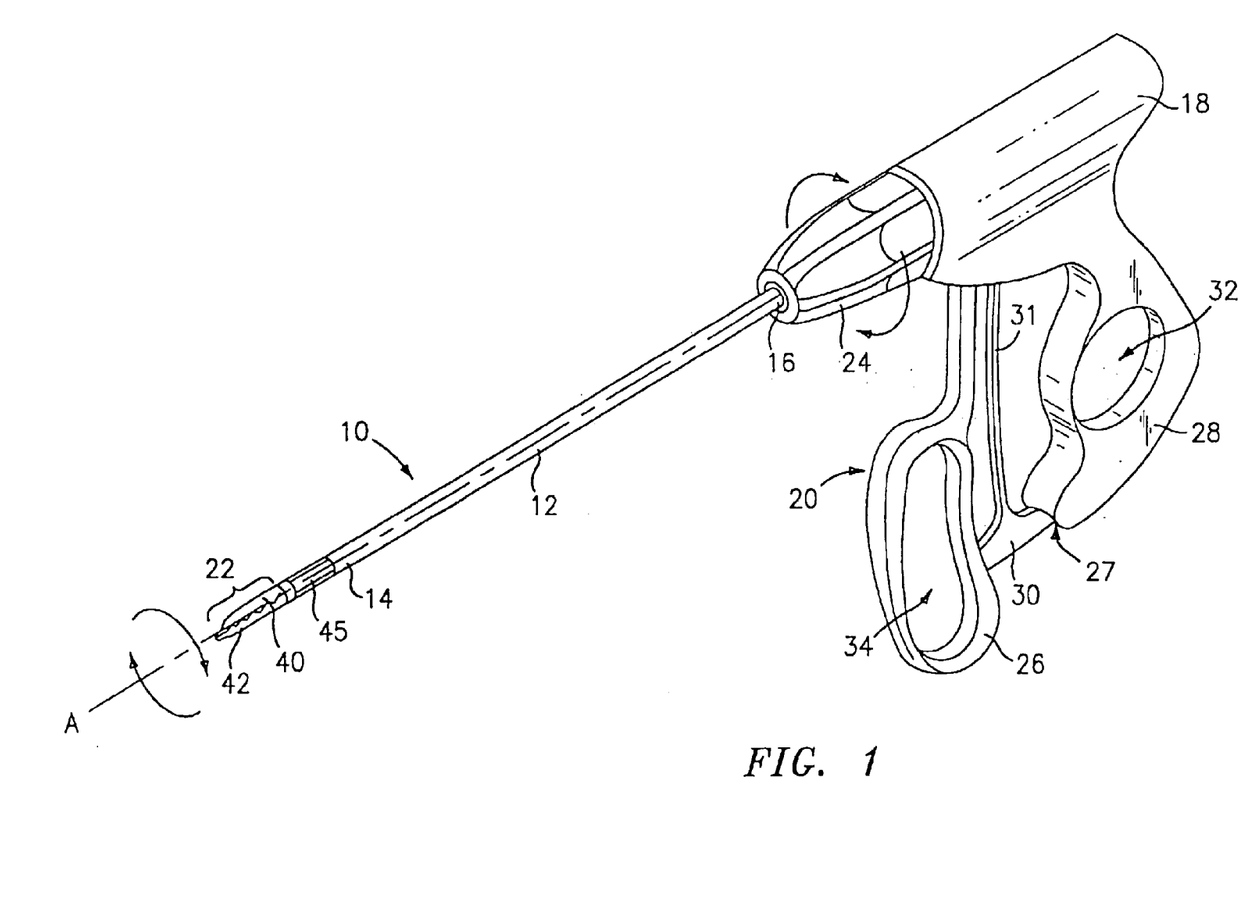
FIG. 1 is a perspective view of a forceps according to the present disclosure.

Referring now to FIG. 1, a forceps 10 for use with open and/or laparoscopic surgical procedures includes an elongated shaft portion 12 having a proximal end 16 and a distal end 14. An end effector assembly 22 is attached to the distal end 14 of shaft 12 and includes a pair of opposing jaw members 40 and 42. Preferably, a handle portion 18 is attached to the proximal end 16 of shaft 12 and includes an activator assembly 20 for imparting movement of the jaw members 40 and 42 from an open position wherein the jaw members 40, 42 are disposed in spaced relation relative to one another, to a clamping or closed position wherein the jaw members 40, 42 cooperate to grasp tissue 51 therebetween.

Activator assembly 20 includes a movable handle 26 having an aperture 34 defined therein for receiving at least one of the operator's fingers and a fixed handle 28 having an aperture 32 defined therein for receiving an operator's thumb. Movable handle 26 is selectively moveable from a first position relative to fixed handle 28 to a second position in closer proximity to the fixed handle 28 to close jaw members 40, 42. Preferably, fixed handle 28 includes a channel 27 which extends proximally for receiving a ratchet 30 which is coupled to movable handle 26. This structure allows for progressive closure of end effector assembly 22 as well as locking engagement of opposing jaw members 40, 42.

In some cases it may be preferable to include other mechanisms to control and/or limit the movement of handle 26 relative to handle 28 such as, e.g., hydraulic, semi-hydraulic and/or gearing systems.

Handle portion 18 may also include a rotation knob 24 for controlling the rotational movement of the end effector assembly 22 about a longitudinal axis "A" of the elongated shaft 12. Preferably, the ratio of rotation of the knob 24 to the end effector assembly 22 is 1:1, however, it is contemplated that gearing structure may be incorporated to increase or decrease the rotational ratio depending upon a particular purpose.

Figure 2:
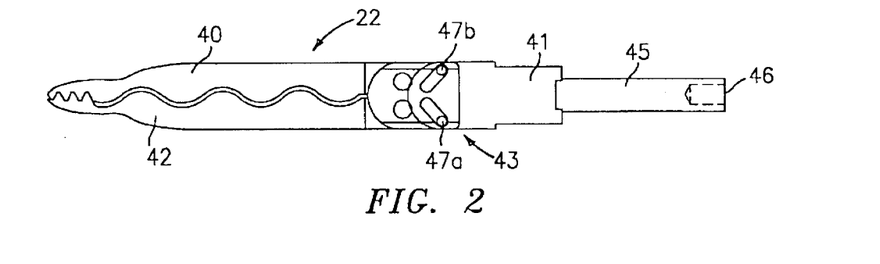
FIG. 2 is an enlarged, side view of a pair of jaw members of the forceps of FIG. 1 shown in closed configuration.
Figure 3:
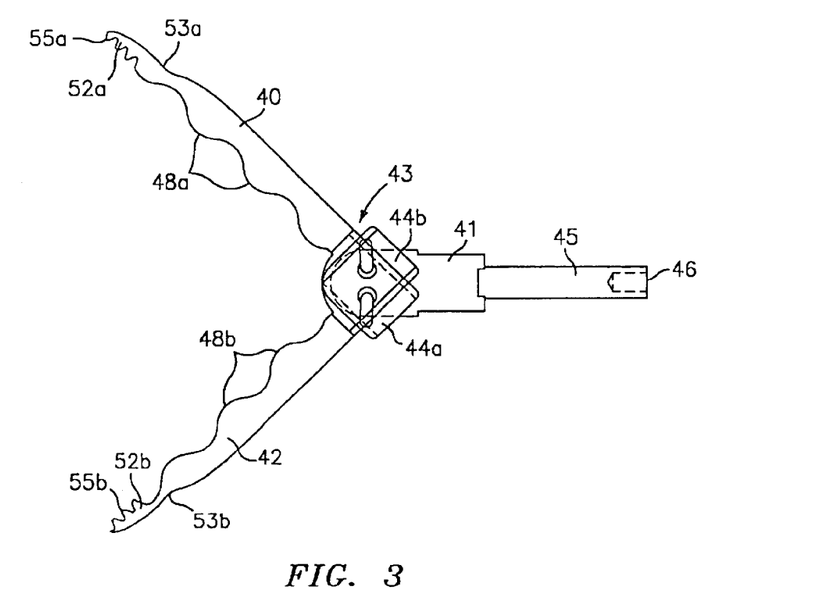
FIG. 3 is an enlarged, side view of a pair of jaw members of the forceps of FIG. 1 shown in open configuration.
Figures 4, 5:
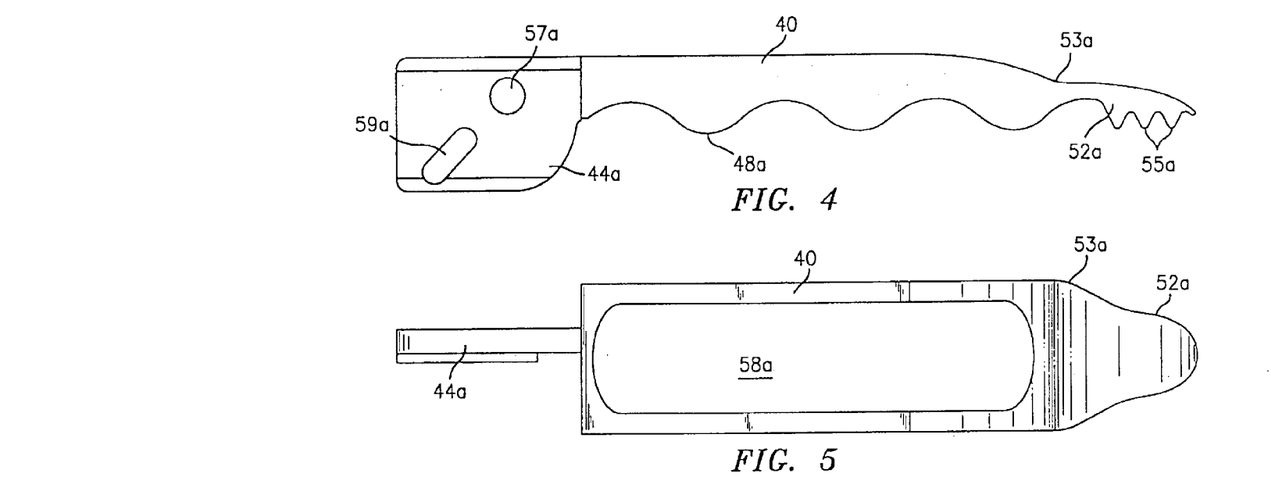
FIG. 4 is an enlarged, side view of the upper jaw member of FIG. 3 showing a plurality of clamping and manipulating wave portions disposed along an inner facing surface thereof.
FIG. 5 is an enlarged, top view of the upper jaw member of FIG. 3 showing a fenestrated portion disposed therethrough.

FIGS. 2 and 3 show enlarged views of the end effector 22 which includes a first or upper jaw member 40 and a second or lower jaw member 42 which are disposed in opposing relation about pivot assembly 43. End effector 22 also includes a pivot housing 41 and a rod 45 having a coupler 46 which matingly engages the distal end 14 of shaft 12. The pivot assembly 43 includes a first pivot portion 44a attached to the upper jaw member 40 and a second pivot portion 44b attached to the lower jaw member 42 which are each affixed to the pivot housing 41 by pins 47a and 47b, respectively. As explained in detail above, movement of handle 26 effects movement of the jaw members 40, 42 about the pin assembly 43 from an open position (FIG. 3) to a closed position (FIG. 2).

Each jaw member 40, 42 includes a plurality of wave forms disposed along its inner facing surface which cooperate to engage tissue 51 therebetween. Preferably, each jaw member 40 and 42 includes clamping wave portions 48a and 48b and manipulating wave portions 52a and 52b, respectively (FIG. 3). The clamping and manipulating wave portions 48b, 58b, respectively, disposed on the inner facing surface of the lower jaw member 42 are complimentary (out of phase) to the clamping and manipulating wave portions 48a, 52a, respectively, of the upper jaw member 40 thus, the upper and lower jaws interfit in the closed position (FIG. 2).

In one embodiment of the present disclosure, the clamping wave portions 48a, 48b are disposed along a proximal portion of each jaw member's 40, 42 length and the manipulating wave portions 52a, 52b are tapered at or about step 53a, 53b to facilitate dissection. In some cases, however, it may be preferable to adjust the length of the clamping wave portions 48a, 48b relative to the manipulating wave portions 53a, 53b to suit a particular purpose. Preferably, the radius of curvature of the clamping wave portions 48a, 48b is greater than the radius of curvature of the manipulating wave portions 52a, 52b. More particularly, the manipulating wave portions 52a, 52b preferably include a plurality of small peaks 55a and 55b which facilitate dissection and delicate positioning of tissue. The clamping wave portions 48a, 48b, on the other hand, preferably include larger, more undulating, wave patterns to improve atraumatic grasping of large structures and to increase surface area contact. In another embodiment of the present disclosure, the small peaks 55a, 55b are filleted to reduce trauma to the tissue 51. It is also envisioned that by filleting peaks 55a, 55b and the areas between successive peaks 55a, 55b, areas of high current densities which typically occur at or along sharp edges/points and which may cause tissue damage, e.g., tissue sticking and charring, will be reduced.

FIG. 49 show enlarged views of the jaw members 40, 42 of the present disclosure. More particularly, FIG. 46 show upper jaw member 40 which includes clamping wave portions 48a and manipulating wave portions 52a which extend in a longitudinal fashion along the inner facing surface of jaw member 40. Likewise, FIGS. 7–9 show lower jaw member 42 which includes complimentary clamping wave portions 48b and manipulating wave portions 52b which also extend in a longitudinal fashion along the inner facing surface jaw member 42.

Jaw members 40, 42 also include apertures 57a and 57b, respectively, and slots or cams 59a and 59b which are each disposed within respective pivot portions 44a and 44b and mount jaw members 40, 42 about pivot pins 47a and 47b, respectively to pivot housing 41 (see FIGS. 2 and 3). Preferably, slots 59a, 59b effect opposing linear movement of the jaw members 40, 42 about pins 47a, 47b. However, in some cases it may be preferable to manufacture slots or cams 59a, 59b with a different shape, e.g., harmonic, parabolic and/or cycloidal, to move the jaw members 40, 42 in a different and/or more prescribed manner.

As seen best in FIGS. 5, 6, 8 and 9 each jaw member 40, 42 also includes an elongated fenestration 58a, 58b disposed therethrough which is preferably dimensioned about the same length as the clamping wave portion 48a, 48b of each jaw member 40, 42. It is envisioned that when tissue 51 is grasped between clamping wave portions 48a, 48b, the fenestration feature of the jaw members 40, 42 will cause the tissue 51 to inundate fenestrations 58a, 58b thus providing better atraumatic holding/grasping of the tissue 51.

Figure 6:
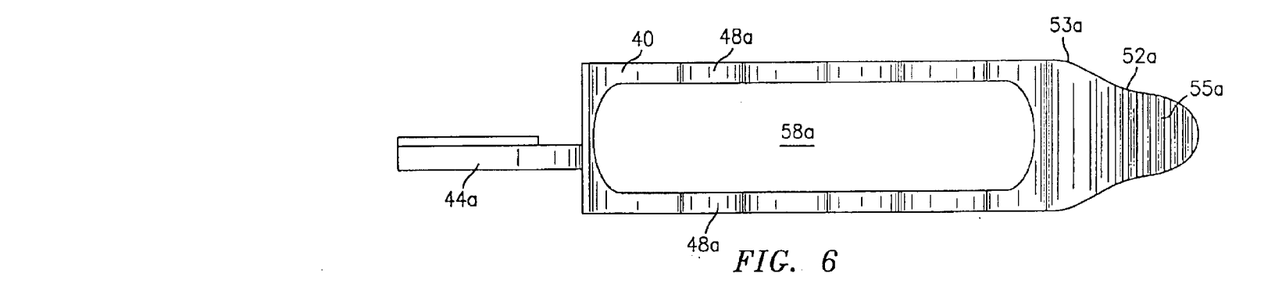
FIG. 6 is an enlarged, bottom view of the upper jaw member of FIG. 3 showing the undulating wave forms disposed on the inner facing surface of the upper jaw member of FIG. 3.
Figures 7, 8:
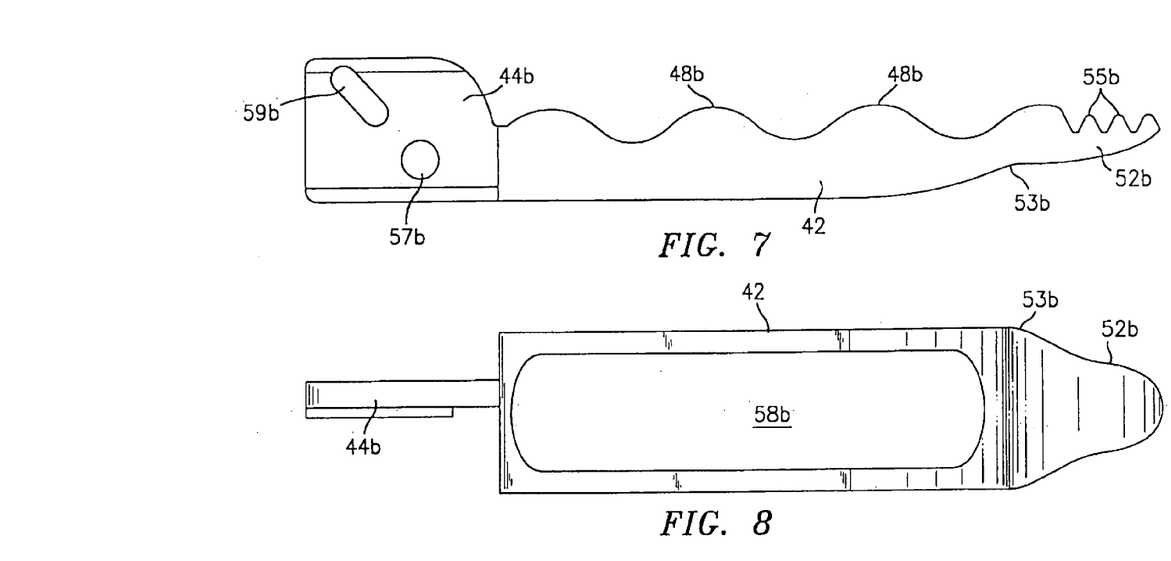
FIG. 7 is an enlarged, side view of the lower jaw member of FIG. 3 showing a plurality of clamping and manipulating wave portions disposed along an inner facing surface thereof.
FIG. 8 is an enlarged, top view of the lower jaw member of FIG. 3 showing a fenestrated portion disposed therethrough.
Figure 9:
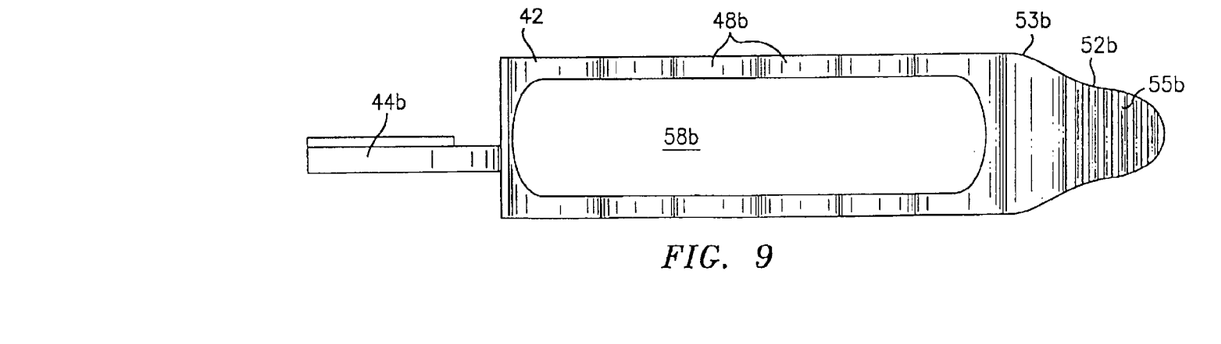
FIG. 9 is an enlarged, bottom view of the lower jaw member of FIG. 3 showing the undulating wave forms disposed on the inner facing surface of the lower jaw member which compliment the wave forms of the upper jaw member.

FIGS. 6 and 9 illustrate one possible wave pattern for the opposing inner facing surfaces of the upper jaw member 40 and the lower jaw member 42, respectively. It is envisioned that any plurality of wave patterns can be utilized depending upon a particular purpose. For example, with this embodiment, the wave pattern includes clamping wave portions 48a, 48b which run longitudinally along either side of fenestration 58a, 58b and manipulating wave portions which also run longitudinally from step 53a, 53b to the distal end of each jaw member 40, 42. It is envisioned that providing wave patterns on the clamping wave portion 48a, 48b of the inner facing surfaces of the jaw members 40, 42 will require more of the tissue 51 to circumnavigate these waves/curves thus providing better grasping power of the tissue 51. In addition, the fenestration feature will also require the tissue 51 to inundate the fenestrations 58a, 58b causing the tissue 51 to hold on an additional or second plane.

Figure 10:
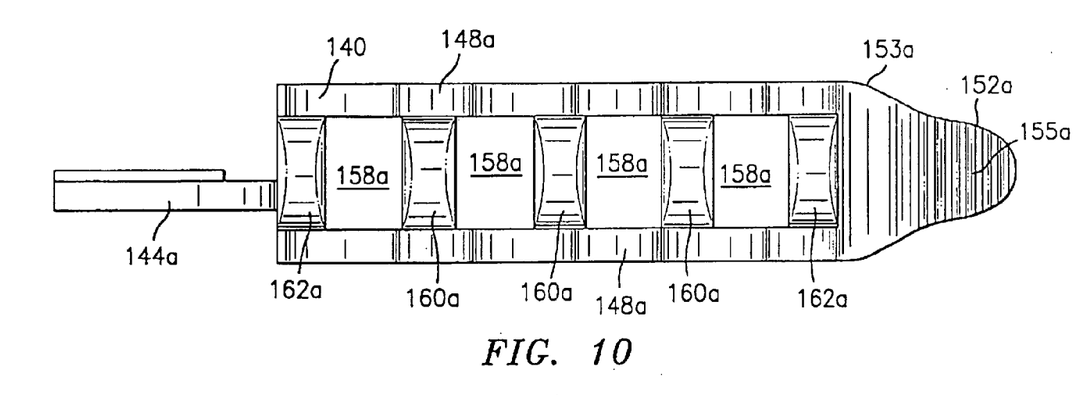
FIG. 10 is an enlarged, bottom view of another embodiment of the present disclosure showing a plurality of wave forms disposed both longitudinally and transversely along the inner facing surface of the upper jaw member.
Figure 11:
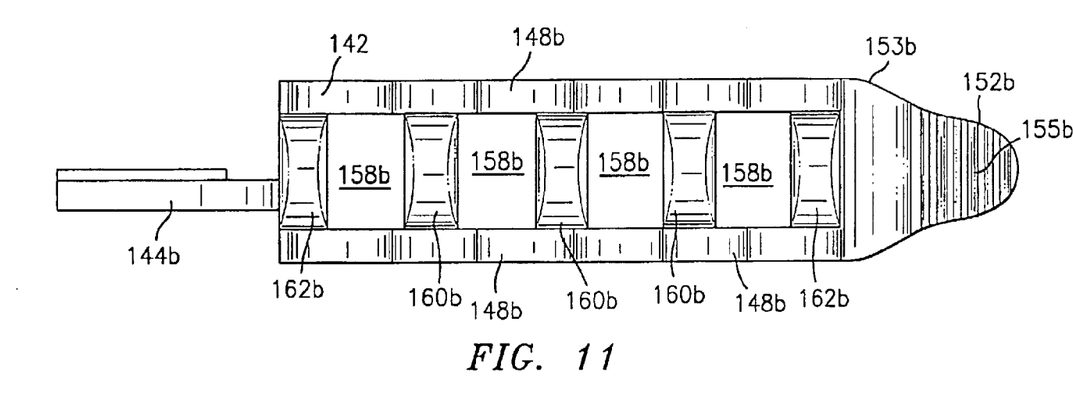
FIG. 11 is an enlarged, bottom view of the complimentary lower jaw member of FIG. 10.

FIGS. 10–13b show other wave patterns which can be formed on the inner facing surfaces of the jaw members 40, 42. For example, FIGS. 10 and 11 show a plurality of fenestrations 158a disposed along the inner facing surfaces of each jaw member 40, 42 and the wave pattern includes both longitudinally disposed clamping wave portions 148a, 148b and transversely disposed wave portions 160a, 162a and 160b, 162b. More particularly, the clamping wave portions 148a, 148b run longitudinally along either side of the plurality of fenestrations 158a, 158b and the manipulating wave portions 152a, 152b run longitudinally from step 153a, 153b to the distal end of each jaw member 140, 142. Wave patterns 160a, 160b run transversely between fenestrations 158a, 158b and wave patterns 162a, 162b run transversely at either end of the plurality of fenestrations 158a, 158b.

Figures 12, 13A, 13B:
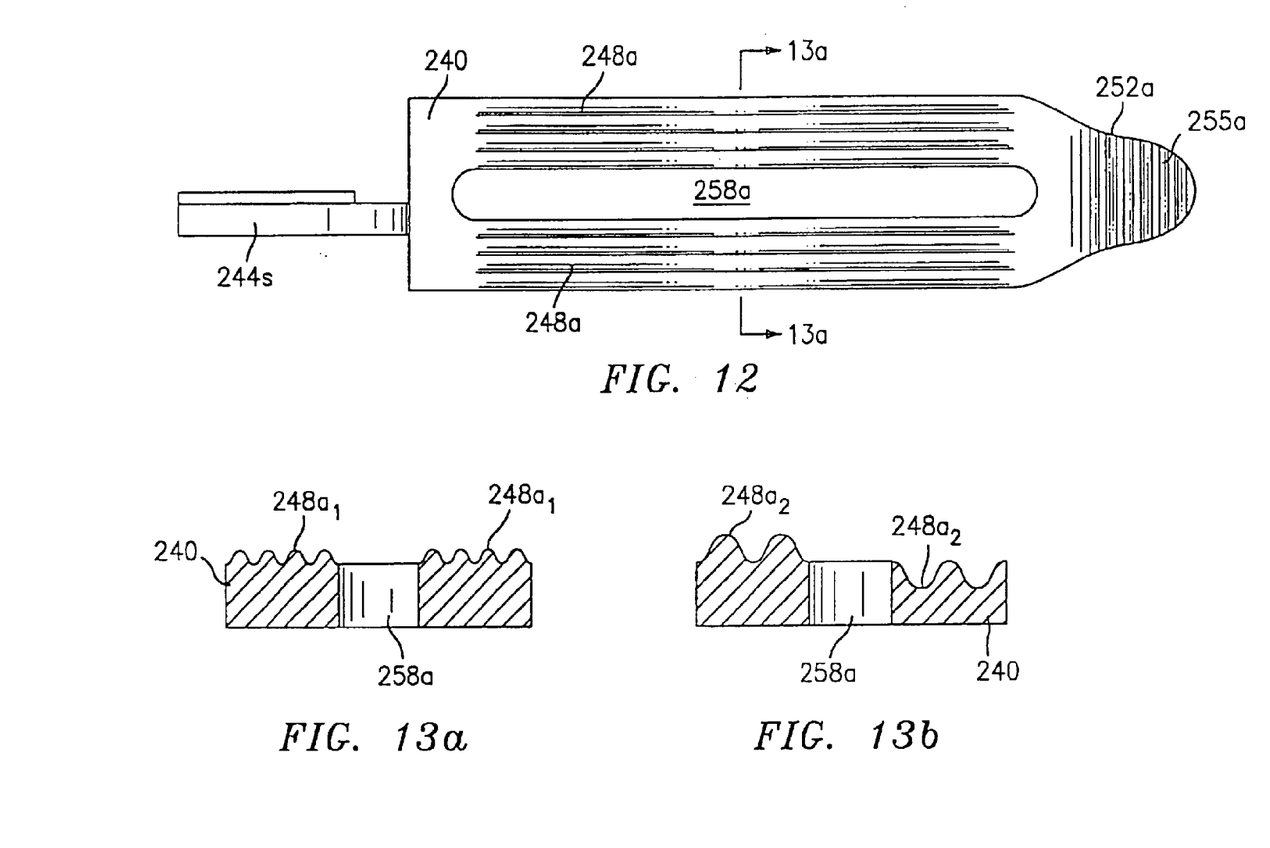
FIG. 12 is an enlarged, bottom view of another embodiment of the present disclosure showing a plurality of wave forms disposed transversely along the inner facing surface of the upper jaw member.
FIG. 13a is an enlarged, frontal view in cross-section taken along line 13a—13a of FIG. 12.
FIG. 13b is an enlarged, frontal view in cross-section of another embodiment of the present disclosure showing an alternative transverse wave pattern disposed along the inner facing surface of the upper jaw member.

FIGS. 12, 13a and 13b show yet other possible wave patterns which can be employed along the inner facing surfaces of the jaw members. For illustrative purposes, the upper jaw member 240 is shown but it is envisioned that the lower jaw member of this embodiment is simply complimentary to the upper jaw member 240. FIGS. 12 and 13a show clamping wave portions $248a_1$ having a transverse wave pattern (a wave pattern which extends axially across upper jaw member 240) disposed on either side of fenestration 258a. FIG. 13b shows another possible transverse wave pattern for the clamping wave portions $248a_2$ along the inner facing surface of the upper jaw member 240. It is envisioned that all of the these wave patterns and accompanying fenestrations will provide better atraumatic grasping of the tissue 51 along the various planes and some wave patterns may be better suited for particular purposes.

Figure 14:
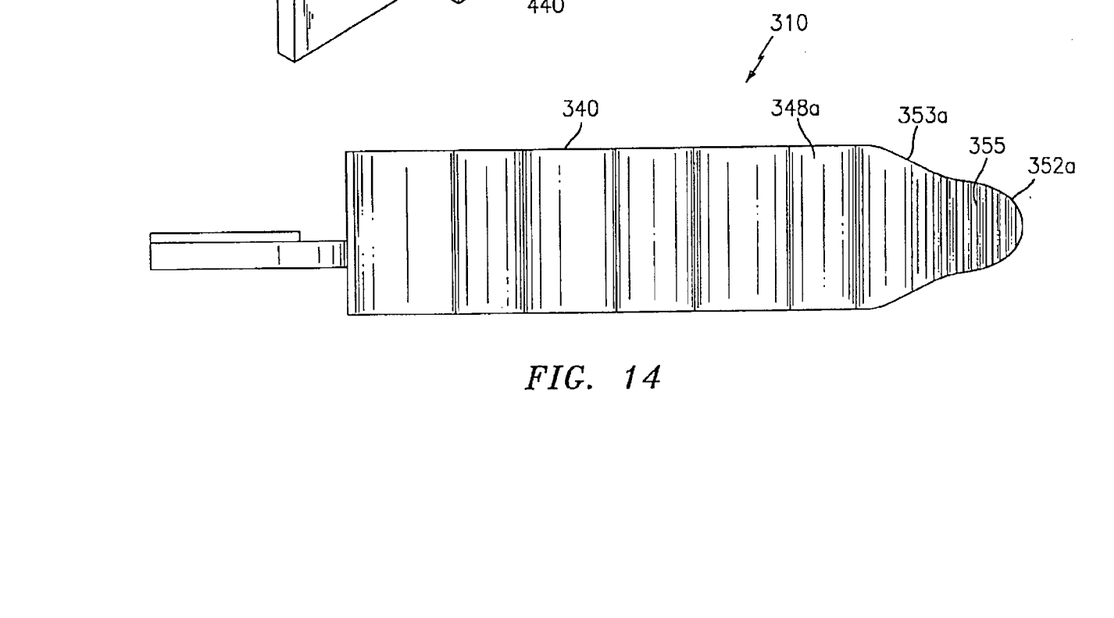
FIG. 14 is an enlarged, bottom view of another embodiment of the present disclosure showing a plurality of wave forms disposed longitudinally along the inner facing surface of the upper jaw member.

FIG. 14 shows a forceps 310 having yet another wave pattern employed along the inner facing surfaces of the jaw members. Clamping wave portion 348a includes a longitudinal wave pattern generally disposed across the inner facing surface of the jaw member 340 and manipulating wave portion 352a extending from step 353a to the distal end of upper jaw member 340. In this embodiment, the fenestration feature is not included.

Figure 15:
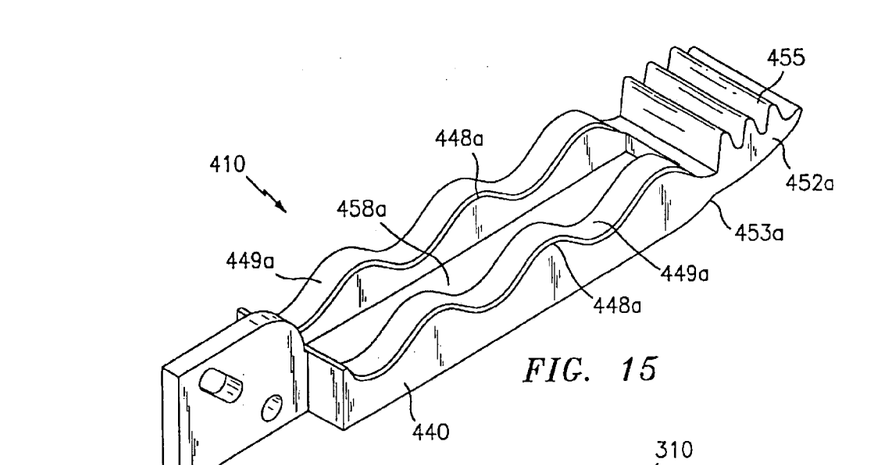
FIG. 15 is an enlarged, perspective view of another embodiment of the present disclosure showing the upper jaw member having electrodes disposed on the inner facing surface of the upper jaw member.
Figure 16:
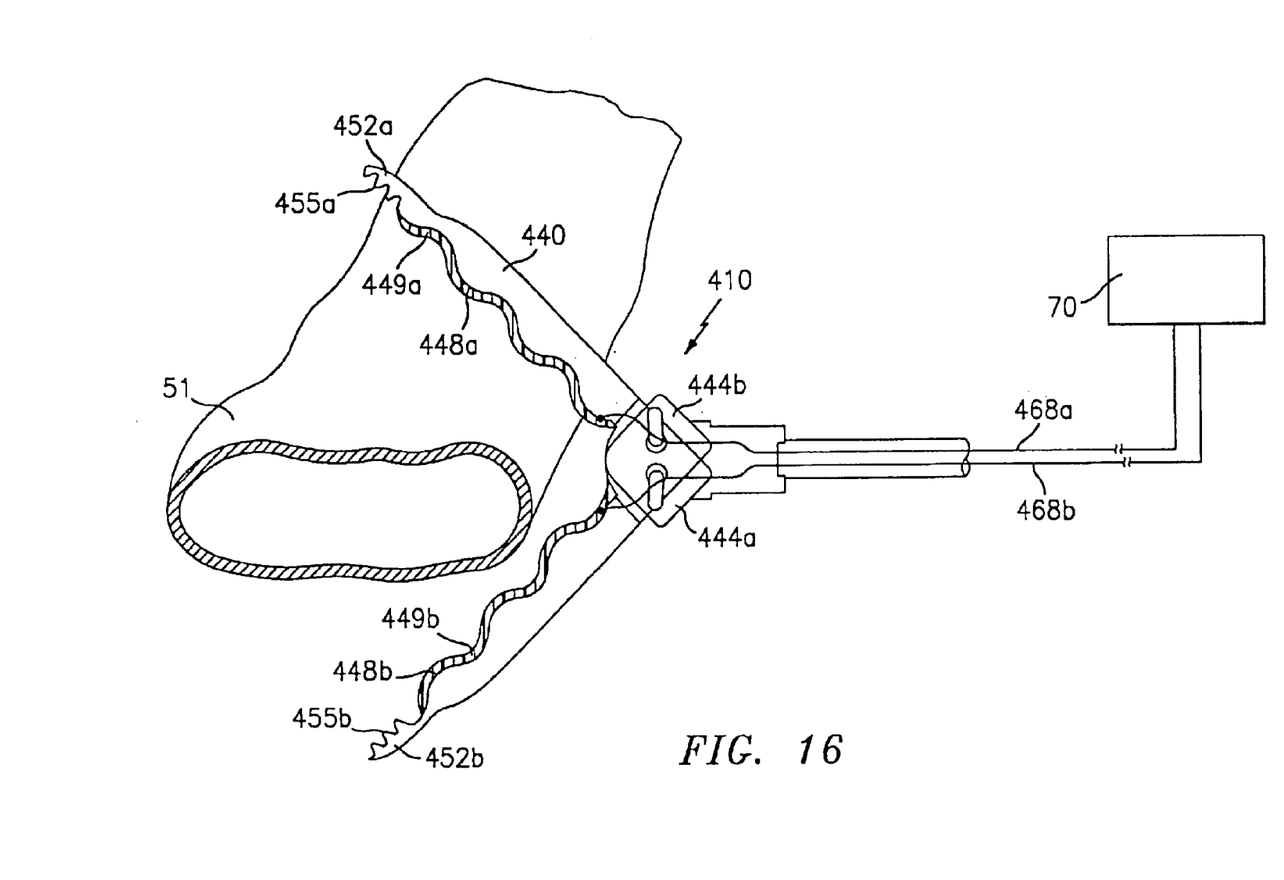
FIG. 16 is a side view showing two jaw members in open configuration prior to engagement about a tubular vessel.
Figure 17:
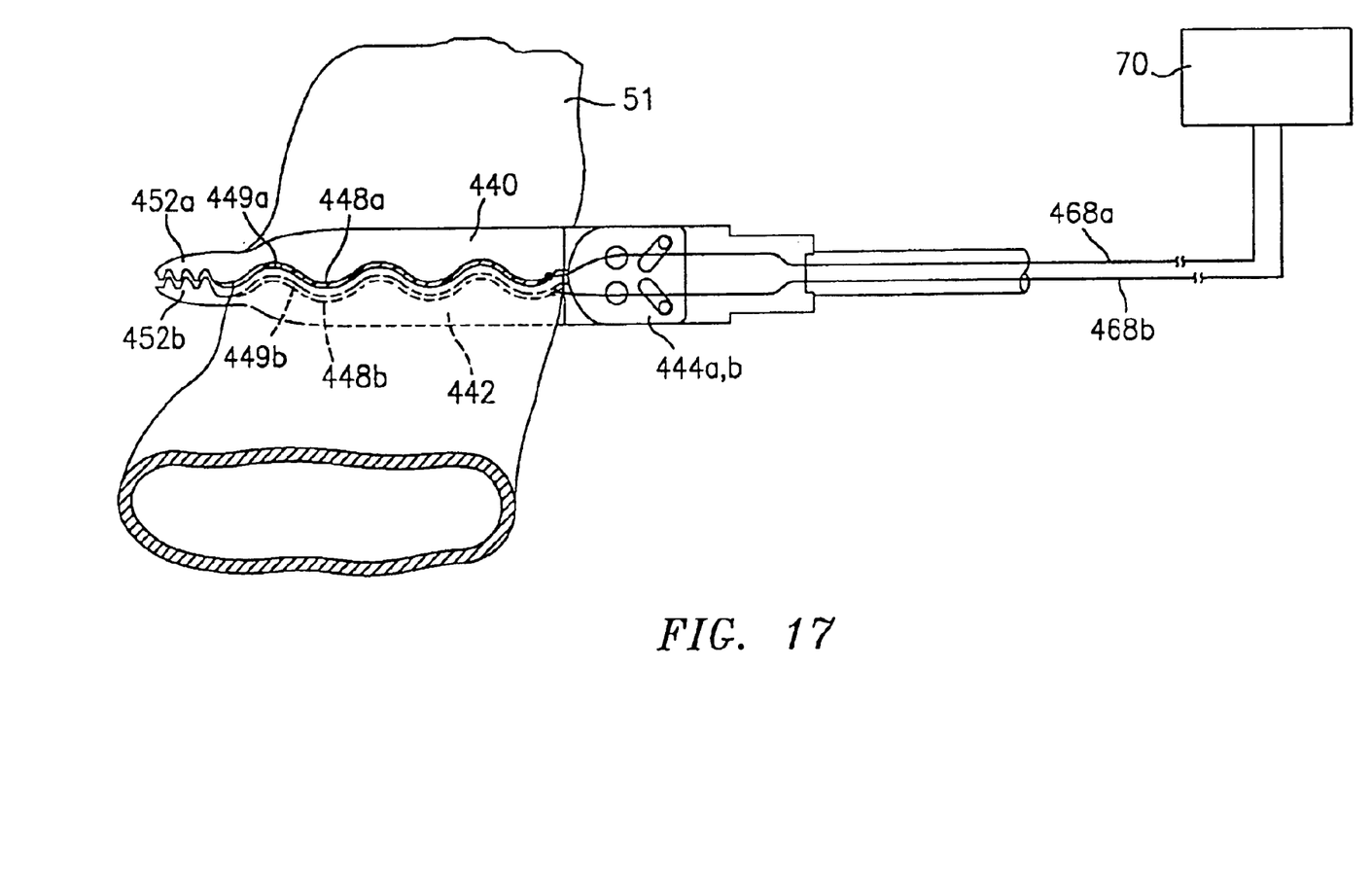
FIG. 17 is a side view showing the two jaw members of FIG. 16 in closed configuration about a tubular vessel.

FIGS. 15–17 illustrate a bipolar forceps 410 according to the present disclosure which includes a plurality of coagulating wave portions 448a, 448b and a plurality of manipulating wave portions 452a, 452b disposed along the inner facing surface of each jaw member 440, 442. Preferably, the forceps also includes at least one electrode 449a, 449b disposed on the inner facing surface of each jaw member 440, 442 and at least one fenestration 458a, 458b disposed through each jaw member 440, 442. As mentioned above with the other embodiments of the present disclosure, it is envisioned that the fenestration feature of the jaw members 440, 442 causes the tissue 51 to inundate fenestrations 458a, 458b providing better atraumatic holding/grasping of the tissue. It is envisioned that one or perhaps several of the aforedescribed wave patterns may also be used to improve vessel sealing and/or coagulation with this particular embodiment of the present disclosure.

For the purposes herein the term coagulating is defined as a process of desiccating tissue wherein the tissue cells are ruptured and dried. Vessel sealing is defined as the process of liquefying the collagen in the tissue so that it crosslinks and reforms into a fused mass.

As best seen in FIGS. 16 and 17, each electrode 449a, 449b is electrically coupled to an electrosurgical generator 70 by a cable 468a, 468b, respectively. The generator 70 imparts different electrical potentials to each electrode 449a, 449b and since tissue 51 is a conductor of electrical energy, when the upper and lower jaw members, 440, 442, respectively, grasp tissue 51 therebetween, the electrical energy is transferred through the tissue 51. By controlling the intensity, frequency and duration of the electrosurgical energy applied to the tissue 51, and, to a certain extent, by controlling the mechanical clamping pressure applied to the tissue 51, the surgeon can either cauterize, coagulate/desiccate and/or cut tissue and/or simply reduce or slow bleeding.

The electrodes 449a, 449b are disposed along the coagulating wave portions 448a, 448b of the jaw members 440, 442 and are generally shaped according to the contours and undulating patterns of the coagulating wave portions 448a, 448b. Preferably, portions of the inner facing surfaces of each jaw member 440, 442 are nonconductive and/or semi-conductive to control or eliminate undesirable current densities which may convene at these locations. For example, an insulative coating could be applied to the small peaks 455a, 455b to reduce the possibility of electrical shorting when the forceps 410 is sealing/coagulating tissue 51 grasped in the coagulating wave portions 448a, 448b of the jaw members 440, 442. Moreover, various metal alloys could be employed to add non-stick characteristics to the bipolar forceps 410.

In addition to rendering the forceps 410 atraumatic and improving its overall grasping features by the provision of fenestrations and various wave patterns disposed along the inner facing surfaces of the jaw members 440, 442, the wave features of the forceps 410 increase the overall surface area for welding vessels and other anatomical structures which is believed to provide superior tissue sealing effects.

In use, the surgeon manipulates handle 26 to advance the activator assembly 20 and move jaw members 440, 442 to the open position wherein the jaw members 440, 442 are disposed in spaced relation relative to one another to receive tissue 51 therebetween. The surgeon then manipulates handle 26 to impart movement of the jaw members 440, 442 about pivot portions 444a, 444b to close the inner facing surfaces of the jaw members 440, 442 about tissue 51.

Depending upon the surgeons particular purpose, the surgeon can close either the coagulating wave portions 448a, 448b and/or the manipulating wave portions 452a, 452b about the tissue 51 to coagulate/seal/cut and/or delicately manipulate the tissue 51. If the surgeon's purpose is to coagulate seal/cut the tissue 51, then after the jaw members 440, 442 are closed about the tissue 51, the surgeon then applies electrosurgical energy to the tissue 51. By controlling the intensity, frequency and duration of the electrosurgical energy applied to the tissue 51, the surgeon can either cauterize, coagulate/desiccate and/or cut tissue and/or simply reduce or slow bleeding.

From the foregoing and with reference to the various figure drawings, those skilled in the art will appreciate that certain modifications can also be made to the present disclosure without departing from the scope of the present disclosure. For example, it is envisioned that various longitudinal, transverse wave patterns can be formed on the jaw members depending upon a particular purpose. In addition, the shape and size of the fenestrations may also be altered to meet a particular purpose.

Although it is preferable to form the upper and lower jaw members such that they are complimentary and intermesh with one another, in some cases it may be preferable to include non-complimentary portions depending upon a particular purpose. Moreover, it may be preferable to offset the upper jaw member fenestrations from the lower jaw member fenestrations.

Although it is preferable to vertically align the electrodes on the bipolar version of the forceps, in some cases it may be preferable to offset the opposing electrodes relative to one another either longitudinally or transversely to suit a particular purpose.

In addition, it may be preferable to add other features to the forceps of the present disclosure, e.g., an articulating assembly to axially displace the end effector assembly relative to the elongated shaft.

There have been described and illustrated herein several embodiments of a forceps having wavelike opposing jaws for clamping, grasping, manipulating, cauterizing, coagulating/desiccating and/or cutting vascular tissue in an atraumatic fashion. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. In an electrosurgical forceps having first and second jaw members operatively attached adjacent a distal end thereof and a handle assembly adjacent a proximal end thereof, the jaw members being movable between an open position and a closed position, the improvement comprising opposing inner facing surfaces each having a plurality of separate and different wave forms disposed thereon, the first of said plurality of different wave forms including large undulating wave forms with substantially large radiuses of curvature and substantially smooth complementary surfaces and the second of said plurality of different wave forms including small teeth-like wave forms with filleted peaks disposed thereon configured to reduce areas of high current concentration during electrical activation.

2. A forceps according to claim 1 wherein a clamping portion of each of the jaw members is wider than a manipulating portion of each of the jaw members.

3. A forceps according to claim 1 wherein the plurality of wave forms of each of the first and the second jaw members are longitudinally disposed on the inner facing surface of each jaw member.

4. A bipolar electrosurgical forceps, comprising:
a shaft portion having a proximal end and a distal end;
first and second jaw members pivotally attached to the distal end of the shaft by a pivot assembly, each of the jaw members comprising an opposing inner facing surface having a plurality of separate and different wave forms disposed thereon, the opposing inner facing surfaces capable of engaging tissue therebetween;
the plurality of wave forms disposed on the inner facing surface of the second jaw member being complimentary to the plurality of wave forms disposed on the inner facing surface of the first jaw member;

the inner facing surface of at least one of the jaw members having at least one fenestrated portion disposed therethrough; and a handle portion attached to the proximal end of the shaft, the handle portion having an activator assembly disposed therein for imparting movement of the first and second jaw members from a first open position wherein the jaw members are disposed in spaced relation relative to one another to a second clamping position wherein the jaw members cooperate to grasp tissue therebetween, wherein the first of said plurality of different wave forms including large undulating wave forms with substantially large radiuses of curvature and substantially smooth complementary surfaces and the second of said plurality of different wave forms including small teeth-like wave forms with filleted peaks disposed thereon configured to reduce areas of high current concentration during electrical activation.

5. A forceps according to claim 4 wherein the inner facing surfaces of both of the jaw members have at least one fenestrated portion disposed therethrough.

6. A forceps according to claim 5 wherein at least one of the fenestrated portions of the inner facing surface of the first jaw member is vertically aligned with at least one of the fenestrated portions of the inner facing surface of the second jaw member.

7. A forceps according to claim 4 wherein at least one portion of the inner facing surface of each of the jaw members is coated with a non-stick coating.

8. A forceps according to claim 4 wherein at least one portion of each of the inner facing surfaces of each of the jaw members is nonconductive.

9. A forceps according to claim 4 wherein at least one portion of each of the inner facing surfaces of each of the jaw members is semi-conductive.

* * * * *